(12) United States Patent
Fitz et al.

(10) Patent No.: US 11,771,570 B2
(45) Date of Patent: Oct. 3, 2023

(54) SECURING ARRANGEMENT FOR A PROSTHETIC HAND ON A FOREARM SHAFT AND PROSTHESIS SYSTEM

(71) Applicant: Otto Bock Healthcare Products GmbH, Vienna (AT)

(72) Inventors: Stefan Fitz, Vienna (AT); Klaus Weissmayer, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 214 days.

(21) Appl. No.: 16/468,647

(22) PCT Filed: Dec. 12, 2017

(86) PCT No.: PCT/EP2017/082440
§ 371 (c)(1),
(2) Date: Jun. 11, 2019

(87) PCT Pub. No.: WO2018/121983
PCT Pub. Date: Jul. 5, 2018

(65) Prior Publication Data
US 2019/0290453 A1    Sep. 26, 2019

(30) Foreign Application Priority Data
Dec. 27, 2016  (DE) .......................... 102016125724.9

(51) Int. Cl.
*A61F 2/54*   (2006.01)
*A61F 2/80*   (2006.01)
(Continued)

(52) U.S. Cl.
CPC ................. *A61F 2/54* (2013.01); *A61F 2/58* (2013.01); *A61F 2/583* (2013.01); *A61F 2/585* (2013.01);
(Continued)

(58) Field of Classification Search
CPC ...... A61F 2/54; A61F 2/76; A61F 2/80; A61F 2002/7837; A61F 2002/543; B25J 15/0095
See application file for complete search history.

(56) References Cited

U.S. PATENT DOCUMENTS 2,427,974 A * 9/1947 Otterman ................ A61F 2/585
279/904
3,798,680 A * 3/1974 Prout ...................... A61F 2/588
623/61
(Continued)

FOREIGN PATENT DOCUMENTS

DE  102010053114 A1   5/2012
DE  102011110099 A1 * 2/2013 ............. A61F 2/586
(Continued)

OTHER PUBLICATIONS

Grace Fabrication Plates. O&P Edge Magazine. (Year: 2014).*
(Continued)

*Primary Examiner* — Christie Bahena
(74) *Attorney, Agent, or Firm* — Holland & Hart LLP (57) ABSTRACT

A securing arrangement of a prosthetic hand on a forearm socket with a receiving frame that can be fixed to the forearm socket, the prosthetic hand being fixed to said receiving frame, wherein the receiving frame is designed to feature radially-directed openings through which the securing elements protrude. The securing elements positively engage with a proximal connection section of the prosthetic hand.

20 Claims, 6 Drawing Sheets

(51) Int. Cl.
*A61F 2/58* (2006.01)
*A61F 2/76* (2006.01)
*A61F 2/78* (2006.01)
*B25J 15/00* (2006.01)

(52) U.S. Cl.
CPC .................. *A61F 2/76* (2013.01); *A61F 2/80* (2013.01); *A61F 2002/543* (2013.01); *A61F 2002/7887* (2013.01); *B25J 15/0095* (2013.01)

(56) References Cited

U.S. PATENT DOCUMENTS

| | | | | |
|---|---|---|---|---|
| 4,613,331 | A * | 9/1986 | Jacobsen | A61F 2/585 403/90 |
| 5,263,990 | A * | 11/1993 | Handal | A61F 2/80 623/33 |
| 2002/0042659 | A1 * | 4/2002 | Ingimarsson | A61F 2/80 623/33 |
| 2002/0116071 | A1 | 8/2002 | Slemker et al. | |
| 2006/0074493 | A1 * | 4/2006 | Bisbee, III | A61F 2/68 623/26 |
| 2011/0136376 | A1 | 6/2011 | Johnson et al. | |
| 2011/0257765 | A1 | 10/2011 | Evans et al. | |
| 2014/0114439 | A1 | 4/2014 | Iverson et al. | |
| 2014/0228975 | A1 * | 8/2014 | Locker | A61F 2/58 623/65 |
| 2015/0257903 | A1 | 9/2015 | Perry et al. | |

FOREIGN PATENT DOCUMENTS

| | | |
|---|---|---|
| GB | 2498788 A | 7/2013 |
| WO | 2016051138 A1 | 4/2016 |

OTHER PUBLICATIONS

Michael. Modified Joint and Corset Prosthesis Designs. O and P Edge Magazine. (Year: 2004).*
Translation of DE369380C. Artificial arm for violin players. (Year: 1923).*
DE369380C. Artificial arm for violin players. (Year: 1923).*
International Search Report for International Application No. PCT/EP2017/082440, dated Feb. 26, 2018, 3 pages.

* cited by examiner

SECURING ARRANGEMENT FOR A PROSTHETIC HAND ON A FOREARM SHAFT AND PROSTHESIS SYSTEM

TECHNICAL FIELD

The invention relates to a securing arrangement of a prosthetic hand on a forearm socket with a receiving frame that can be attached to the forearm socket, the prosthetic hand being attached to said receiving frame, as well as a prosthesis system with a forearm socket and a prosthetic hand fixed to said prosthesis system via the securing arrangement. In particular, the invention relates to the securing arrangement for a so-called transcarpal hand, which is used with a treatment if a long residual forearm has been preserved.

BACKGROUND

Prosthetic hands, which should be understood to also mean passive prosthetic hands, active prosthetic hands, purely cosmetic prosthetic hands or other gripping devices, such as so-called hooks or similar, are fixed via a forearm socket on a prosthesis user. The forearm socket generally features a dimensionally stable outer shell, which is adapted more or less exactly to the contour of the forearm. A liner or padding may be arranged between the residual forearm and the outer shell in order to offset any volume fluctuations in the residual limb, to create an interface or to provide padding against compressive forces. Various other mounting devices, such as a vacuum generator or a belt and sleeves, may be used to fix the forearm socket to the residual limb and, where appropriate, also to the arm. The actual prosthetic hand is fixed to the forearm socket via a securing arrangement, such as a bayonet system or a screw connection, at the distal end of the forearm socket. The detachable mounting of the prosthetic hand to the forearm socket and the resulting modular structure of the entire prosthesis means that the prosthetic hand can be produced as a separate component. Only the forearm socket is individually adjusted to fit the respective patient. Furthermore, due to the often mechanically complex design and the arrangement of drives and, where applicable, control devices and energy storage systems inside of the prosthetic hand, a single-piece configuration comprising the forearm socket and prosthetic hand is not possible. Despite advancements in miniaturization, the placement of the mechanical and electronic components inside of the prosthetic hand is difficult; energy storage systems, electronic control systems and sensors or mechanical force transmission devices also require space, which is often not available or only available to an insufficient extent, in particular in the case of patients with a low amputation level, such as amputations in the wrist region. This results in the prosthetic hand protruding beyond the natural hand, thereby creating an irregular appearance.

SUMMARY

The task of the present invention is to provide a securing arrangement of a prosthetic hand on a forearm socket as well as a prosthetic device comprising a securing arrangement, a prosthetic hand and a forearm socket, by way of which an improved physiological appearance can be achieved, including for patients with a low amputation level.

This task is solved by a securing arrangement with the features disclosed herein and a prosthesis device with the features also disclosed herein. Advantageous configurations and embodiments of the invention are also disclosed herein in the description and the diagrams.

The securing arrangement of a prosthetic hand on a forearm socket according to the invention, which features a receiving frame that can be fixed to the forearm socket, the prosthetic hand being fixed to said receiving frame, proposes that the receiving frame be designed to feature radially-directed openings, through which the securing elements protrude, wherein said securing elements positively engage with a proximal connection section of the prosthetic hand. The forearm socket completely encloses a residual forearm at least in one distal region, in order to guarantee a stable accommodation of the prosthetic hand. A receiving frame is arranged inside of the forearm socket or on the forearm socket; at least parts of a prosthetic hand or of structural components of a prosthetic hand are accommodated inside said receiving frame. The parts of the prosthetic hand or the components of the prosthetic hand protrude into the receiving frame and are surrounded by the receiving frame either radially or on their outer sides. To fix the prosthetic hand to the receiving frame and thereby also to the forearm socket, radially-directed openings are provided or configured, especially bores or recesses or openings which were already there during the production of the receiving frame, through which the securing elements protrude. These securing elements enable a positive-locking connection with a proximal connection section of the prosthetic hand when the prosthetic hand is fixed to the forearm socket. Once assembled, the connection section of the prosthetic hand faces the forearm socket and serves specifically to mechanically attach the prosthetic hand to the forearm socket. The securing elements enable a reversible attachment of the prosthetic hand to the forearm socket, wherein said securing elements can be radially accessed from outside in such a way that, following the introduction of the connection section into the receiving frame, a positive lock between the connection section and the receiving frame can be achieved. As a result of the radial orientation of the securing elements, there is very little or indeed no need at all for installation space in the longitudinal direction of the forearm socket, such that the prosthetic hand can be fixed very closely to the forearm socket so that it does not protrude far beyond the distal end of the forearm socket in the distal direction. Furthermore, the lateral or radial orientation enables comfortable access to the securing elements, so that the prosthetic hand can be easily removed from a mounted prosthesis socket, for example in order to repair the prosthetic hand or to undertake any adjustments on it.

The receiving frame and the connection section may comprise locking elements that are configured or fixed to them, wherein said locking elements can positively engage, for instance in a similar way to a bayonet mount, wherein a projection is displaced inside a guide and then twisted about a fixed angular range until an end stop is reached. In this position, the connection section is positively locked to the receiving frame. In order to prevent an involuntary release of the lock, securing elements are radially introduced to the positions intended for this specific purpose; they then block a backwards rotation into a release position. This requires that a rotation of the connection element relative to the receiving frame be possible.

A physiologically close configuration of the receiving frame is achieved when said receiving frame comprises an inner contour that is not rotationally symmetrical, in particular an oval or elliptical inner contour, which fundamentally corresponds to the cross-section of the wrist. The fact that the inner contour is not rotationally symmetrical enables a clear allocation of the connection section of the prosthetic hand to the receiving frame and prevents a rotation about an axis in the longitudinal direction of the forearm socket. This allows for a particularly simple production of the receiving frame with a smooth inner contour. The fact that the inner contour is not rotationally symmetrical also enables an effective force transmission across the entire receiving frame, thereby increasing the stability and durability of the securing arrangement. Due to the fact that the inner contour of the receiving frame is not rotationally symmetrical, a precise alignment of the securing elements in relation to the sections of the connection section can occur at predetermined positions of the openings or bores, wherein said sections engage or should be made to engage positively with the securing elements.

The receiving frame may comprise a wall, which extends in the axial direction and is preferably a surrounding wall, from which a ledge extends radially outwards. The ledge that extends radially outwards preferably forms the distal termination of the forearm socket, such that the ledge creates a contact surface for the prosthetic hand or a connection section of the prosthetic hand. The design of the ledge as the distal termination means that, in particular, fiber-reinforced plastics—which are used for the production of a forearm socket—are mechanically protected, thereby improving the durability of the entire prosthesis arrangement. The receiving frame may form the distal termination of a forearm socket that is open at the distal end, such that a passage opening within the inner contour of the receiving frame is formed. The forearm socket is then designed to be tubular, possibly with a tapering in the distal end region, in which the receiving frame surrounds an opening inside and, where applicable, distally. In principle it is also possible for the forearm socket to be distally closed and for the receiving frame to surround the distal end section. The receiving frame can then preferably radially enclose the residual forearm so it requires as little installation space as possible in the longitudinal direction.

Radially protruding projections or undercuts may be configured in the wall of the receiving frame that extends in the axial direction, said projections or undercuts facilitating an attachment of the receiving frame on or in the forearm socket. The attachment of the forearm socket can be facilitated via the projections or undercuts, especially if the receiving frame is laminated in the forearm socket. The projections and/or undercuts may extend in the proximal/distal direction and/or circumferentially in the radial direction in order to prevent a twisting about the longitudinal direction of the forearm socket on the one hand and a pulling-out movement in the distal direction from the forearm socket on the other.

The connection section may be fixed to a base body such that it can be detached, wherein further components of the prosthetic hand are fixed to the base body. For instance, the base body may be a motor drive, a control system, force transmission elements of a drive for prosthetic fingers or moveable components of the prosthetic hand, as well as bearing elements or axle bearings for fixing moveable components. In the same way as the base body, the connection section may be made of a metal, especially an alloy. The detachable fixing of the connection section to the base body renders it possible to attach different connection sections to the base body, such that standard base bodies or standard prosthetic hands with different connection sections can be provided in order to enable an individual adjustment to residual arms.

An embodiment of the invention proposes that the connection section be attached such that it can be twisted and fixed to the base body in the respective twisted position, in order to achieve a rotary alignment of the base body and therefore of the distal component of the prosthetic hand on the forearm socket. This renders an improved alignment of the prosthetic hand relative to the forearm socket and thus to the forearm of the patient possible. Production inaccuracies can be offset or physiological particularities compensated for.

The connection section may comprise at least one elongated hole, in particular a partially circular elongated hole, which interacts with a fixing element attached to the base body, said fixing element being accommodated in the elongated hole, and can thus be fixed or clamped upon reaching the desired position. In principle it is also possible for the base body to feature an elongated hole which is designed in the shape of the movement to be carried out relative to the connection section. Alongside a partially circular configuration of the elongated hole, by way of which a rotary orientation is achieved, a different shape of the elongated hole may also be provided so as to enable translational displacement from the base body towards the connection section, in addition to a rotary adjustment. In general, purely linear elongated holes may also be provided. Specifically, the fixing element is designed as a screw in order to allow for a simple and reversible fixing of the connection section relative to the base body.

An embodiment of the invention proposes that the connection section be attached to the base body using a central screw in order to guarantee a basic positioning of the base body on the connection section before a final orientation of the connection section in relation to the base body is conducted via a twisting and/or displacement and fixing of the respective position via the fixing elements or the fixing element.

The connection section may feature ledges that extend towards the forearm socket or a correspondingly oriented, preferably surrounding, wall. The ledges or the wall therefore extend in the proximal direction. The ledges are positioned correspondingly to the openings in the receiving frame and overlap with the openings when the connection section is arranged inside the receiving frame. This renders it possible to introduce the mounting element or the securing elements into the ledges, or to conduct a corresponding fixing to the ledges. Alternatively to the configuration with individual, at least two, ledges, a wall can be arranged or configured on the connection section, wherein at least one thread is incorporated or arranged in said wall, said thread being positioned correspondingly to the opening or the openings in the receiving frame. The at least one mounting element is introduced into the thread so as to enable a fixing. To this end, in an embodiment of the invention, threads are incorporated in the connection section or the connection sections, said threads being positioned correspondingly to the openings in the intended assembled state of the receiving frame in relation to the connection section, such that, by radially introducing screws through the openings into the thread in the ledge or the ledges or the wall of the receiving frame, the receiving frame is positively and reversibly fixed in the connection section.

The connection section can be mounted on a base plate of the base body to enable a modular construction of the base body. The arrangement of the connection section in relation to the base body is achieved via the base plate; it is also possible for the remaining components of the prosthetic hand to be reversibly coupled with the connection section via the base plate. This renders it possible to attach different components of a prosthetic hand or different models or sizes of a prosthetic hand to a base plate in order to be able to provide a predetermined interface to a connection section. Alternatively to a multi-piece design of the base body, consisting of a base plate and support, the base body may also be designed as a single piece.

The support is preferably positively coupled with the base plate, for instance it is screwed on or fixed via a dovetail guide with an additional fixing. The base body may also be positively coupled with the base plate, for instance it is screwed on or fixed via a dovetail guide with an additional fixing.

The connection section may feature an outer contour that is designed correspondingly to the inner contour of the receiving frame in order to facilitate as clear an alignment as possible of the connection section in relation to the receiving frame and also to effect an even introduction of force via as uniform an placement as possible of the connection section on the receiving frame.

The receiving frame is preferably laminated in the forearm socket and can be additionally secured on the forearm socket via the securing elements. The securing elements are preferably designed as screws or bolts.

At least one passage for cables or other data lines or force transmission devices may be configured in the connection section and in the base body, said passage leading from the forearm socket to the prosthetic hand, so as to enable either a mechanical or electronic activation of the prosthetic hand.

The connection section preferably comprises an inner free space that is encircled by the ledges, such that further components of the prosthetic hand can be arranged, such as an energy storage system, control components, sensors, plugs or cables, inside the ledges or inside the area that is encircled by the ledges.

The invention also relates to a prosthesis system or a prosthesis device with a prosthetic hand, which is attached to a forearm socket via the securing arrangement described above.

BRIEF DESCRIPTION OF THE DRAWINGS

In the following, examples of embodiments of the invention will be explained in more detail by way of the attached drawings. They show.

DETAILED DESCRIPTION

Figure 1:
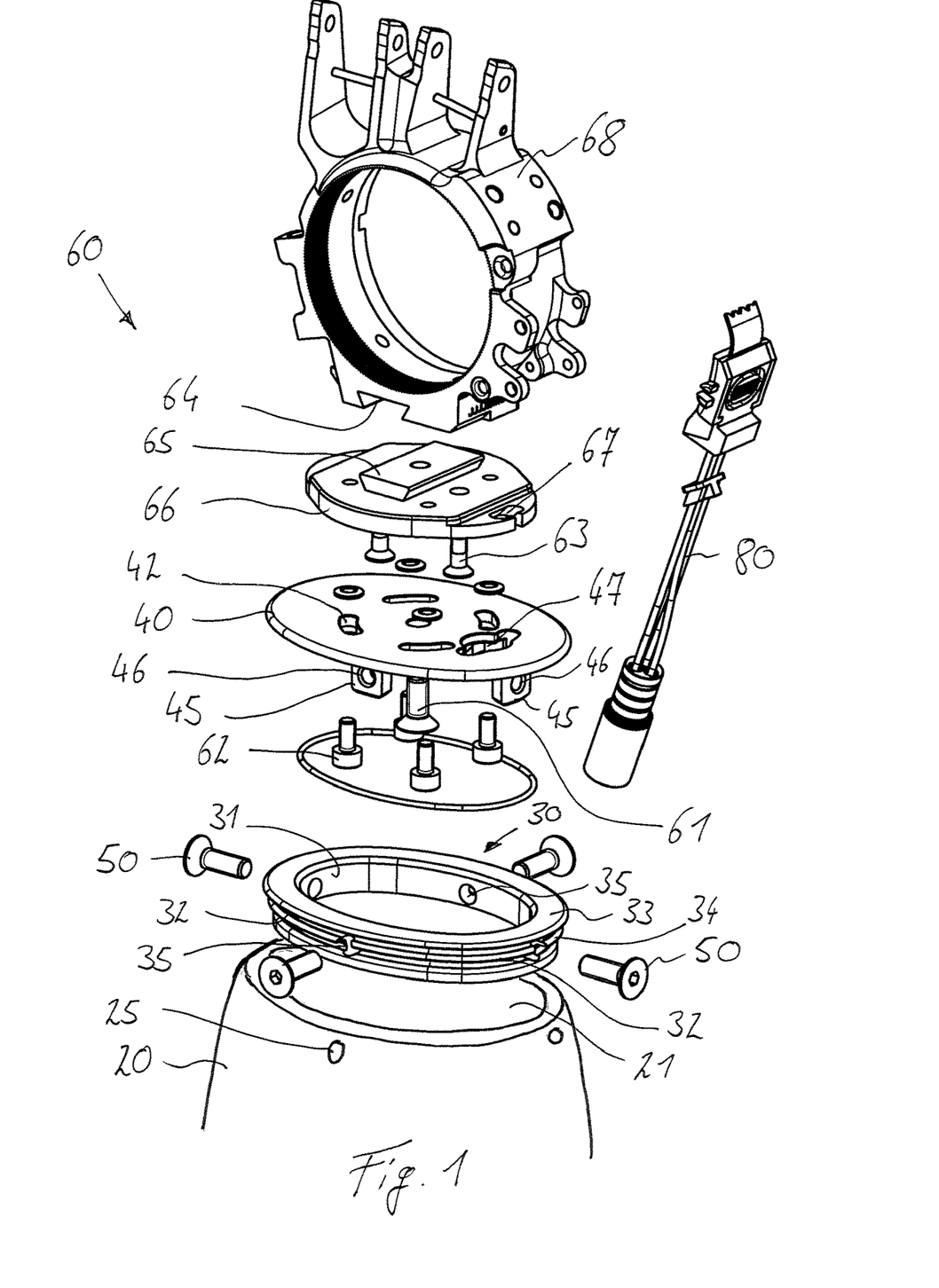
FIG. 1—an exploded view of a securing arrangement of a prosthetic hand.

FIG. 1 shows an exploded view of the basic components of a prosthetic hand, which shall be depicted in more detail later, with an indicated forearm socket 20, which is designed to accommodate a receiving frame 30. In the distal region depicted, the forearm socket 20 is designed with a closed circumference and, as a distal end section, comprises a passage opening 21, inside of which a receiving frame 30 can be and is installed. The receiving frame 30 has an oval outer contour and an oval inner contour 31, wherein the outer contour generally corresponds to the inner contour in the region of the opening 21 of the prosthesis socket 20. The shape is approximately equivalent to a cross-section of the residual limb in the wrist region. The receiving frame 30 comprises a wall 32 that extends in the axial direction, i.e. in the longitudinal direction of the forearm socket 20, from which a radially-outward protruding ledge 33 extends, said ledge being a distal termination. The ledge may fit closely on the distal terminal edge of the forearm socket 20, thereby forming the distal termination of the forearm socket 20. Alternatively, the receiving frame 30 can also engage in the prosthesis socket 20 in such a way that it is flush with the distal edge.

Openings or bores 25 are configured or introduced inside the prosthesis socket 20, wherein said openings or bores go through the wall of the prosthesis socket 20 and render it possible to screw in or push through securing elements 50 in the form of screws. Inside the receiving frame 30, bores 35 or openings 35 are introduced or configured in the wall 32, said bores or openings being positioned correspondingly to the bores or openings 25 in the prosthesis socket. Following the lamination of the receiving frame 30, the openings will penetrate from the inside out, for instance, in order to convey the exact position of the openings 25. Threads may be configured or arranged in the bores 35. The screws 50 can thus protrude through the outer wall of the prosthesis socket 20 and the wall 32 of the receiving frame 30, such that they protrude into the inner contour 31 of the receiving frame 30 once they have been screwed or pushed in. In principle, it is also possible that the securing elements 50 or screws are not guided through the prosthesis socket 20 when the receiving frame 30 protrudes distally beyond the end of the prosthesis socket 20. In the example of an embodiment depicted, the inner contour 31 is not rotationally symmetrical, but rather oval or ellipsoid. In principle it is also possible to configure the inner contour 30 to be rotationally symmetrical or to select the shape of the inner contour 3 to be polygonal.

Figure 6:
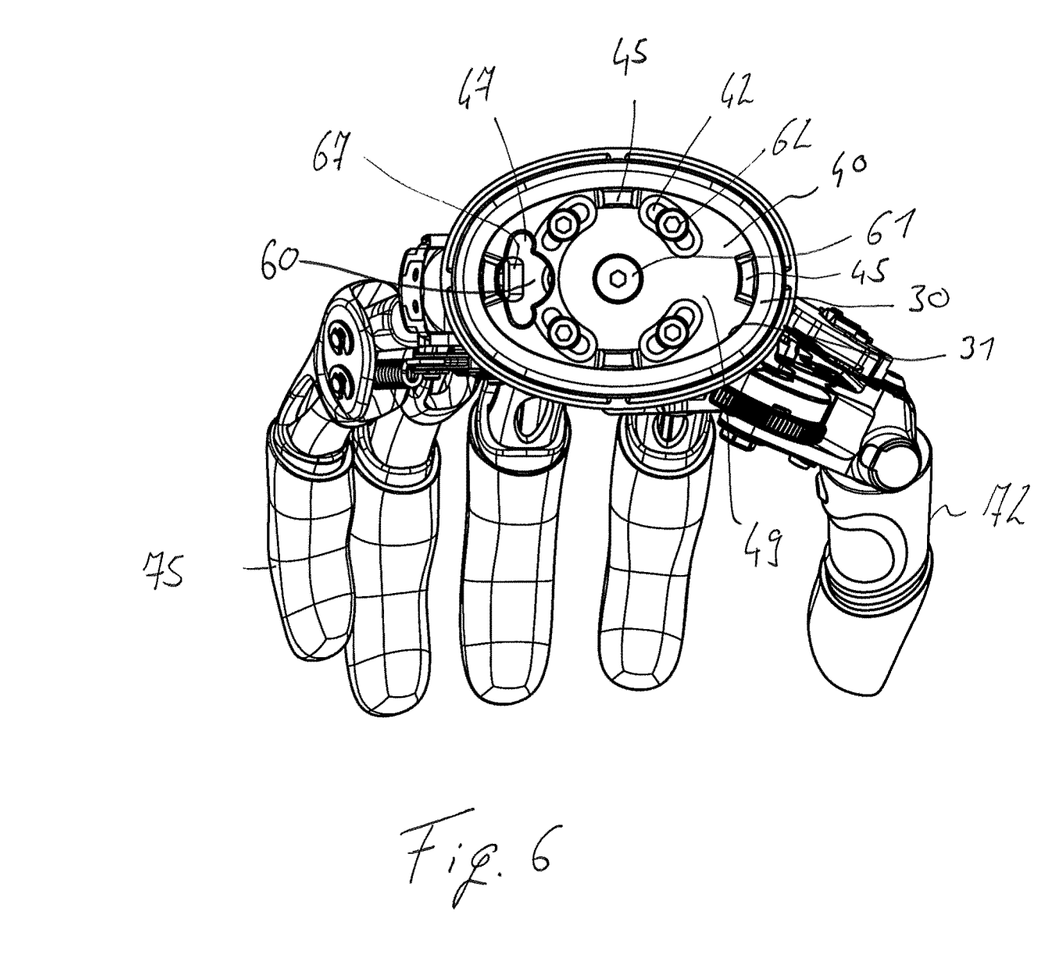
FIG. 6—a bottom view in a neutral position.
Figure 7:
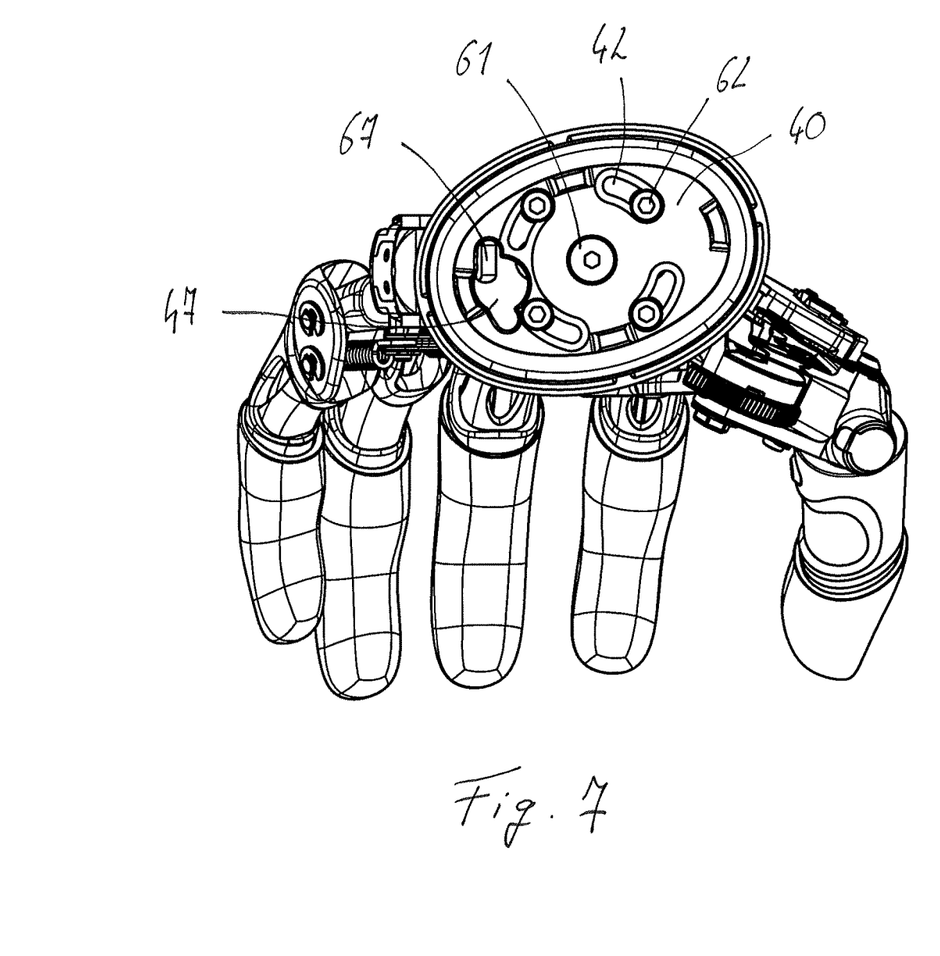
FIG. 7—a bottom view of a prosthetic hand that has been twisted clockwise.
Figure 8:
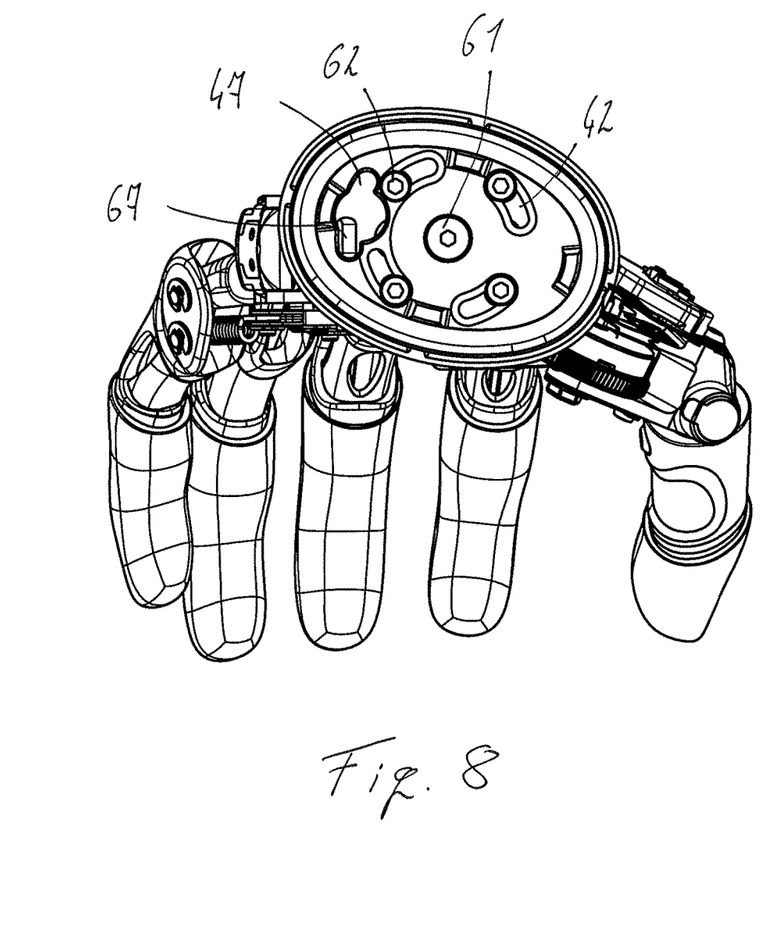
FIG. 8—a bottom view of a prosthetic hand that has been twisted anti-clockwise.

FIG. 1 also shows a support 68 of a prosthetic hand. Additional elements of the prosthetic hand may be arranged on the support 68, for example a motor drive in the central recess and movably mounted prosthetic fingers or a prosthetic thumb at the outer bearing positions. The support 68 comprises a dovetail mount 64 on its proximal lower side, which enables a positive lock with a guide 65, wherein said guide is correspondingly configured as a dovetail. Centrally arranged inside the dovetail guide 65, which is arranged or configured on a base plate 66, is a bore with a thread, into which a centrally arranged screw 61 can be screwed. The screw 61, which is also depicted in FIGS. 6 to 8, is screwed in from the proximal direction, i.e. from below in the orientation of the diagram depicted, through a connection section 40 into the base plate 66, such that the base plate 66 can be assembled with the connection section 40, which is designed as a plate and features downward-extending projections 45. In addition, two screws 63 are guided laterally through the base plate 66 alongside the dovetail guide 65 and screwed into screw holes—not visible—in the support 68 on both sides of the dovetail mount 64, in order to create a positive-locking and reversible connection between the support 68 and the base plate 66. A passage 67 is designed on one side of the base plate 66, through which the cables 80 can be passed during assembly so as to create a connection of electric or electronic components or energy storage systems in the region of the prosthesis socket 20 to the sensors or electrical consumers inside the prosthetic hand. The passage 67 is open at the sides, thereby allowing the cables 80 to be laterally introduced and guided through. The base plate 66 is also oval-shaped, wherein the passage 67 in the base plate 66 has a side opening at an outer vertex.

The plate-shaped connection section 40 with the downward—i.e. proximally—protruding projections 45 are arranged proximally to the base plate 66 and fixed to the base plate 66 with four screws 62, which form the fixing elements for the connection section 40 on the base plate 66. The fixing elements 62 engage in four threaded bores inside the base body 66 and protrude through the plate-shaped connection section 40, in which elongated holes 42 are arranged. To mount and position the connection section 40 on the base plate 66, the central screw 61 is first of all guided through the central bore in the connection section 40, also oval; it then engages with the thread inside the base plate 66. The support 68 may be fixed to the base plate 66 in advance using the screws 63. The connection section 40 is then mounted, if applicable after cables 80 have been guided through a passage 67 configured in the connection section 40, said passage enabling an overlap with the passage 47 in the base plate 66 in the mounted state. If the base plate 66 is screwed onto the connection section 40 and the cables 80 have been guided through the passages 47, 67, the base plate 66 can be twisted relative to the connection section 40 about the central screw 61 in such a way that a rotary alignment in relation to one another is possible. For the final assembly, the fixing elements 62 in the form of screws are guided through the elongated holes 42 and screwed into the threads of the base plate 66. In the example of an embodiment shown, the elongated holes 42 are designed as partially circular elongated holes 42, which are arranged about the central screw 61 on a common circumference, such that a twisting of the base plate 66 remains possible until the fixing elements 62 are screwed in and tightened in order to clamp the base plate 66 to the connection element 40.

In addition to a partially circular configuration of the elongated holes 42 about a central screw 61, it is also possible to forego the central screw 61 and to design the elongated holes 42 such that their contour is not partially circular, so as to enable a translation of the base plate 66 relative to the connection section 40, as well as a rotation. The central screw 61 may also be guided in an elongated hole, such that both a rotation and a displacement of the base plate 66 in relation to the connection section 40 is possible when a central screw 61 is provided for preassembly purposes.

In the example of an embodiment shown, four projections 45 are configured on the lower side of the connection section 40, said projections being designed as tabs or blocks, in which threads 46 are configured. The projections 45 are slightly set back from the outer circumference of the plate-shaped connection section 40 and correspond to the inner contour 31 of the receiving frame 30. In the mounted state, the outer sides of the projections 45 may lie flat on the inner contour 31 of the receiving frame 30 or be positioned very close to it. The projections 45 with the threads 46 are positioned such that, when in the mounted state, they align with the openings 35 in the wall 33, such that the securing elements 50 pass through the openings 35 in the receiving frame 30 and engage in the threads 46. This enables a rotary and translational attachment of the connection section 40 to the receiving frame 30 and thereby of the prosthetic hand to the prosthesis socket 20.

The receiving frame 30 may be laminated inside the prosthesis socket 20. The openings 25 can be designed to be so large that the screw heads in the prosthesis socket 20 are countersunk, where applicable the screw heads may also lie flat against the wall 32, such that no positive lock occurs between the prosthesis socket 20 and the receiving frame 30 via the screws. The projections 45 preferably lie flat on the inner contour 31 of the receiving frame 30, wherein a free space is designed inside the projections 45, in which cables, electronic components or other electric or mechanical components may be arranged, wherein these are arranged around or between the fixing elements 62

Figure 2:
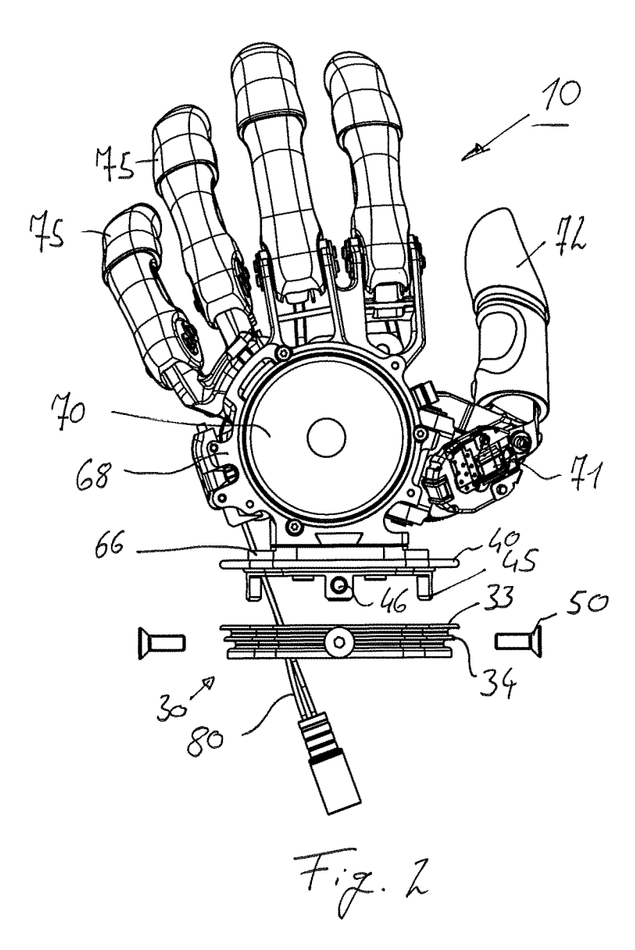
FIG. 2—a top view of a diagram of a partially assembled prosthetic hand with a receiving frame.

FIG. 2 shows the prosthetic hand 10 with the securing arrangement in a partially mounted state; the prosthesis socket 20 is not depicted for the sake of clarity. In the side view according to FIG. 2, which depicts a top view of the back of the hand, as in the side view according to FIG. 3, which depicts a view of the outer edge of the hand, it is clear that the receiving frame 30 has an elliptical shape and that a projection 34 is configured on the outer side of the wall 32, wherein said projection renders an improved positive-locking connection inside the prosthesis socket—not depicted—possible. A smooth lateral wall 32 would make lamination and a restraint against a pulling-out movement in the distal direction more difficult; the projection 34 and the resulting undercut created distally and proximally render it possible to create a positive lock of the prosthesis socket 20 and the receiving frame 30.

The prosthetic hand 10 with prosthetic fingers 75, which are mounted on the support 68 such that they can be moved, and the prosthetic thumb 72 with its own drive 71 can be recognized in FIG. 2, as can a central drive 70, which is arranged inside the recess in the support 68. The motor-driven prosthetic fingers 75 and the prosthetic thumb 72 are each actuated about a swivel axis via the central drive 70; the prosthetic thumb 72 can conduct a further swivelling movement about a second swivel axis via the additional drive 71. The support 68 is attached to the base plate 66 by way of the dovetail connection and the screws 63 described in FIG. 1. The connection section 40 is fixed to the base plate 66 via the fixing elements 62 and the central screw 61 such that it can be detached. A total of four projections 45, each with a thread 46 configured in it, protrude from the connection section 40 towards the receiving frame 30, said projections being oriented correspondingly to the openings 35 within the receiving frame 30, thereby enabling a positive-locking, reversible fixing via the securing elements 50 in the form of screws. The cables 80 are guided through the passages 47, 67 in the base plate 66 and the connection section 40 and pass through the interior space between the projections 45, which are arranged opposite one another in pairs, and the free space inside the close-walled oval receiving frame 30, which is open in the centre, such that a connection to an energy storage system and electronic control devices or sensors can be created via a plug connection.

Figure 3:
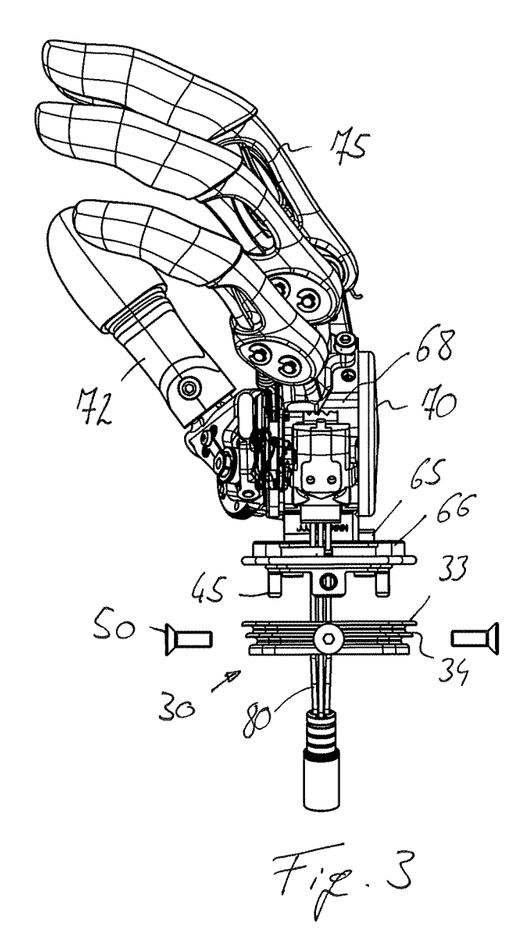
FIG. 3—a side view of an embodiment according to FIG. 2.
Figure 4:
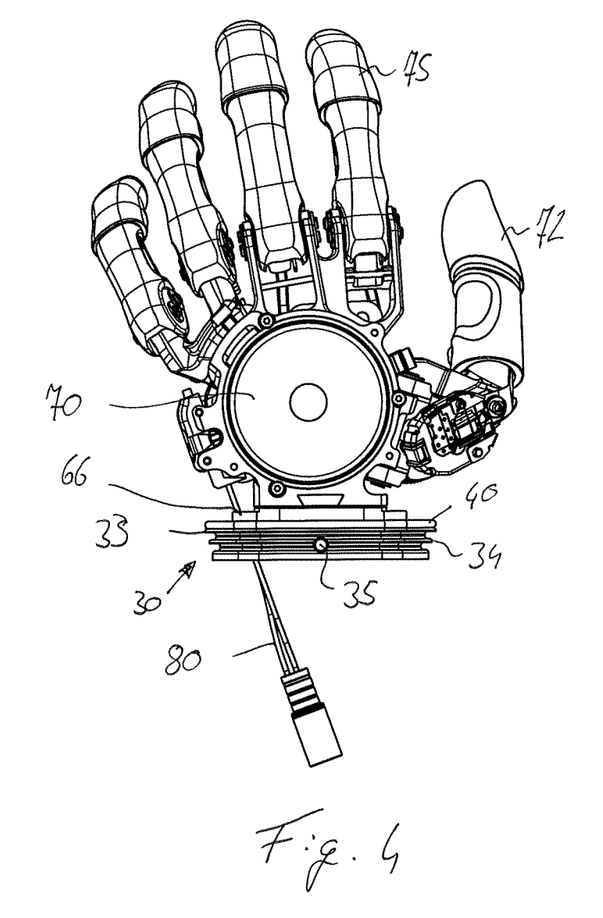
FIG. 4—a top view of a fully assembled prosthetic hand on a receiving frame.
Figure 5:
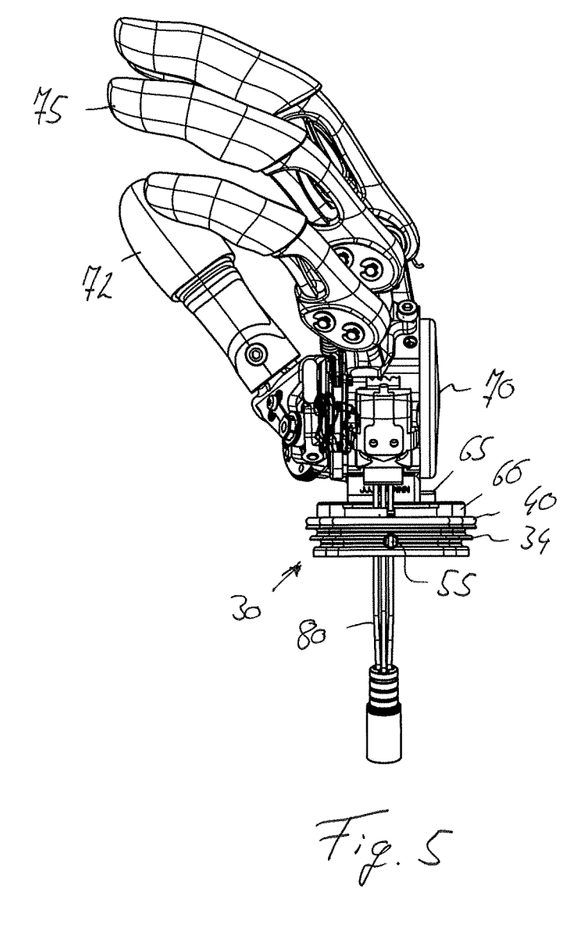
FIG. 5—a side view according to FIG. 4.

FIGS. 4 and 5 depict the prosthetic hand 10 according to FIGS. 3 and 4, also in a partially mounted state, where the connection section 40 has been introduced into the receiving frame 30 with the projections. The securing elements 50 in the form of screws are not depicted; the openings 35 in the form of bores within the receiving frame 30 align with the threads 46 of the projections 45, such that following the introduction and screwing-in of the securing elements 50, a positive lock between the receiving frame and the connection section 40, and therefore also between the prosthetic hand 10 and the prosthesis socket—not depicted—can be created.

FIG. 6 shows the partially mounted state according to FIGS. 4 and 5 in a view from below, in which the proximal end of the prosthetic hand can be recognized. The central screw 61 is clearly visible in the center of the elliptical receiving frame 30; the connection section 40 with the projections 45 is installed within the inner contour 31 of the receiving frame 30; the screws have not yet been screwed in. The fixing elements 62 are arranged in the elongated holes 42 and protrude through them; they are then screwed into the specially provided threads in the base plate 60. Both the passage 47 in the connection section 40 and the passage 67 in the base plate 60 can be recognized; it is also clear that the passages 47, 67 overlap one another. The fixing elements 62 are centrally arranged inside the partially circular elongated holes 42. Inside of the space enclosed by the projections 45, there are no components or structural elements configured on the lower side of the connection section 40, such that the projections 45 and the plate-shaped connection section 40 together form or define a free space 49, in which additional components of the prosthetic hand, mounting tools, cables, control systems, sensors or other structural component can be arranged. The free space 49 can also be designed to feature in a configuration with a wall or a proximally protruding ring wall.

For the rotary alignment of the prosthetic hand 10 relative to the forearm socket 20, the prosthetic hand 10 can be twisted along with the base plate 66 relative to the connection section 40. FIG. 7 depicts the view according to FIG. 6 inside a first prosthetic hand, which has been twisted clockwise to the maximum degree, the fixing elements 62 or screws 62 of which each strike the end of the elongated holes 42. As a result of the enlarged design of the passage 47 compared with the passage 67, the passages 47, 67 still overlap, such that the cables—not depicted—are neither bent nor clamped. FIG. 8 shows the opposite maximum twisted position, in which the fixing elements 62 strike the opposite ends of the elongated holes 42; in this case, the passages 47, 67 also overlap in the connection section 40 and the base plate 66 to enable a collision-free passage of the cables.

As a result of the modular structure of the prosthetic hand with the support 68 and the base plate 66, an exchangeable, positive lock and connection with the securing arrangement can be achieved; this also serves the purpose of mounting on a prosthesis socket. A securing arrangement with the base plate 66, the connection section 40 and the receiving frame 30 can also be individually adjusted. This allows for a combination of different-sized receiving frames 30 with correspondingly designed and adjusted connection sections 40, so as to enable an adjustment to different-sized residual limbs or residual forearms. Following assembly, the fixing elements 62 can generally still be accessed through the prosthesis socket, such that, to conduct a precision adjustment, only the central screw 61 and the fixing elements 62 need be loosened, the base plate 66 twisted relative to the receiving frame 40 and finally the screws 61, 62 tightened again in order to fix the desired position.

The invention claimed is:

1. A securing arrangement of a prosthetic hand on a forearm socket, comprising:
a receiving frame that can be fixed to the forearm socket, the prosthetic hand being fixed to the receiving frame, the receiving frame comprising radially-directed openings, a plurality of securing elements arranged to protrude through the radially-directed openings and engage with a plurality of projections of a proximal connection section of the prosthetic hand, wherein the receiving frame is secured to the forearm socket by the plurality of securing elements that are configured to extend through the forearm socket and into the plurality of projections, wherein the plurality of projections of the proximal connection section of the prosthetic hand are positioned within the receiving frame and each of the plurality of securing elements extends through the forearm socket, the radially-directed openings, and the plurality of projections of the proximal connection section of the prosthetic hand.

2. The securing arrangement according to claim 1, wherein the receiving frame comprises an inner contour that is rotationally non-symmetrical.

3. The securing arrangement according to claim 1, wherein the receiving frame comprises a wall that extends in an axial direction and a ledge that extends radially from the wall.

4. The securing arrangement according to claim 3, wherein the wall comprises radially protruding projections or undercuts.

5. The securing arrangement according to claim 3, wherein the ledge forms a distal termination of the forearm socket.

6. The securing arrangement according to claim 1, wherein the proximal connection section is attached to a base body such that the proximal connection section can be detached.

7. The securing arrangement according to claim 6, wherein the proximal connection section is attached to the base body such that the proximal connection section can be twisted and fixed to the base body.

8. The securing arrangement according to claim 6, wherein the proximal connection section comprises at least one elongated hole and a fixing element accommodated in the elongated hole is fixed to the base body.

9. The securing arrangement according to claim 6, wherein the connection section is configured to be attached to the base body using a central screw.

10. The securing arrangement according to claim 1, wherein the proximal connection section comprises a wall or ledges that extend towards the forearm socket, and the wall or ledges are positioned correspondingly to the openings in the receiving frame.

11. The securing arrangement according to claim 1, wherein threads are incorporated in the connection section which are positioned correspondingly to the openings.

12. The securing arrangement according to claim 1, wherein the base body is designed to be multi-piece and comprises a support and a base plate detachably fixed to said support.

13. The securing arrangement according to claim 12, wherein the base body is positively coupled with the base plate.

14. The securing arrangement according to claim 12, wherein the proximal connection section is fixed to the base plate such that the proximal connection section can be detached.

15. The securing arrangement according to claim 1, wherein the proximal connection section comprises an outer contour that is designed correspondingly to an inner contour of the receiving frame.

16. The securing arrangement according to claims 1, wherein the receiving frame is laminated in the forearm socket.

17. The securing arrangement according to claim 1, wherein the proximal connection section and a base body include at least one passage to receive cables from the forearm socket to the prosthetic hand.

18. The securing arrangement according to claim 1, wherein the proximal connection section comprises an inner free space.

19. A prosthesis system comprising the securing arrangement according to claim 1 and further comprising the forearm socket and the prosthetic hand, wherein the receiving frame is attached to the forearm and the prosthetic hand.

20. A securing arrangement to secure a prosthetic hand on a forearm socket, the securing arrangement comprising:
 a receiving frame configured to be fixed to the forearm socket and the prosthetic hand, the receiving frame comprising:
 radially-directed openings;
 and securing elements protruding through the radially-directed openings and configured to engage with a plurality of projections of a proximal connection section of the prosthetic hand, wherein the receiving frame is secured to the forearm socket by the securing elements that are configured to extend through the forearm socket and into the plurality of projections,
 wherein the plurality of projections of the proximal connection section of the prosthetic hand are positioned within the receiving frame and each of the plurality of securing elements extends through the forearm socket, the radially-directed openings, and the plurality of projections of the proximal connection section of the prosthetic hand.

* * * * *